(12) United States Patent
Hattori et al.

(10) Patent No.: US 8,735,152 B2
(45) Date of Patent: May 27, 2014

(54) METHODS FOR INDUCING CELL DEATH IN PLURIPOTENT STEM CELLS AND DIFFERENTIATED CELLS OTHER THAN CARDIAC MYOCYTES

(75) Inventors: Fumiyuki Hattori, Kobe (JP); Keiichi Fukuda, Tokyo (JP)

(73) Assignees: Daiichi Sankyo Company, Limited, Tokyo (JP); Keio University, Tokyo (JP)

( * ) Notice: Subject to any disclaimer, the term of this patent is extended or adjusted under 35 U.S.C. 154(b) by 0 days.

(21) Appl. No.: 13/260,224

(22) PCT Filed: Mar. 29, 2010

(86) PCT No.: PCT/JP2010/056108
§ 371 (c)(1),
(2), (4) Date: Dec. 21, 2011

(87) PCT Pub. No.: WO2010/114136
PCT Pub. Date: Oct. 7, 2010

(65) Prior Publication Data
US 2012/0094383 A1    Apr. 19, 2012

(30) Foreign Application Priority Data
Mar. 30, 2009  (JP) .................... 2009-083553

(51) Int. Cl.
*C12N 5/00*  (2006.01)
*C12N 5/02*  (2006.01)

(52) U.S. Cl.
USPC ........................................................ 435/373

(58) Field of Classification Search
None
See application file for complete search history.

(56) References Cited

U.S. PATENT DOCUMENTS

| 5,543,316 | A  | * | 8/1996  | Zawadzka et al. | 435/366 |
| 6,589,786 | B1 | * | 7/2003  | Mangano et al.  | 435/372 |
| 2003/0040111 | A1 | * | 2/2003  | Gold et al.     | 435/368 |
| 2005/0189297 | A1 | * | 9/2005  | Bosch et al.    | 210/651 |
| 2008/0241919 | A1 | * | 10/2008 | Parsons et al.  | 435/366 |

FOREIGN PATENT DOCUMENTS

EP    1983042    10/2008

OTHER PUBLICATIONS

European Search Report from EP 10758903.8 dated Jan. 22, 2013.
International Search Report from PCT/JP2010/056108 dated Jun. 7, 2010.
Parekkadan, B. et al, "Osmotic Selection of Human Mesenchymal Stem/Progenitor Cells From Umbilical Cord Blood," Tissue Engineering, vol. 13, pp. 2465-2473, Oct. 2007.

(Continued)

*Primary Examiner* — Blaine Lankford
*Assistant Examiner* — Lauren K Van Buren
(74) *Attorney, Agent, or Firm* — Hunton & Williams LLP

(57) ABSTRACT

The present invention has as its object developing a method that does not involve genomic modification and which yet is capable of inducing cell death in pluripotent stem cells such as embryonic stem cells and induced pluripotent stem cells, as well as in differentiated cells other than cardiomyocytes derived from pluripotent stem cells, but not in cardiomyocytes. It has been revealed that by establishing a method capable of inducing cell death in cells other than cardiomyocytes in a very efficient manner by adding a substance having no recognized inherent toxicity or cell death inducing action to the culture conditions for pluripotent stem cells and non-cardiomyocytes, the stated problem can be solved without relying upon genomic modification.

11 Claims, 15 Drawing Sheets
(15 of 15 Drawing Sheet(s) Filed in Color)

(56) References Cited

OTHER PUBLICATIONS

Huber, I. et al., "Identification and Selection of Cardiomyocytes During Human Embryonic Stem Cell Differentiation," The Journal of the Federation of American Societies for Experimental Biology, vol. 21, No. 10, pp. 2551-2563, Aug. 2007.

Wu, Xu et al., "Small Molecules That Induce Cardiomyogenesis in Embryonic Stem Cells," Journal of the American Chemical Society, vol. 126, No. 6, pp. 1590-1591, Feb. 18, 2004.

Hirata, H. et al. "Coexpression of Platelet-Derived Growth Factor Receptor Alpha and Fetal Liver Kinase 1 Enhances Cardiogenic Potential in Embryonic Stem Cell Differentiation in vitro," Journal of Bioscience and Bioengineering, vol. 103, No. 5, pp. 412-419, May 2007.

Müller, M. et al., "Selection of Ventricular-Like Cardiomyocytes From ES Cells in vitro," The Journal of the Federation of American Societies for Experimental Biology, vol. 14, No. 15, pp. 2540-2548, Dec. 2000.

Schröder, Astrid R.W. et al., "HIV-1 Integration in the Human Genome Favors Active Genes and Local Hotspots," Cell, vol. 110, pp. 521-529, Aug. 23, 2002.

Schuldiner, Maya et al., "Selective Ablation of Human Embryonic Stem Cells Expressing a 'Suicide' Gene," Stem Cells, vol. 21, Issue 3, pp. 257-265, May 2003.

Bieberich, Erhard et al., "Selective Apoptosis of Pluripotent Mouse and Human Stem Cells by Novel Ceramide Analogues Prevents Teratoma Formation and Enriches for Neural Precursors in ES Cell-Derived Neural Transplants," The Journal of Cell Biology, vol. 167, No. 4, pp. 723-734, Nov. 22, 2004.

Choo, Andre B. et al., "Selection Against Undifferentiated Human Embryonic Stem Cells by a Cytotoxic Antibody Recognizing Podocalyxin-Like Protein-1," Stem Cells, vol. 26, Issue 6, pp. 1454-1463, Jun. 2008.

Miller-Keane Encyclopedia and Dictionary of Medicine, Nursing, and Allied Health, Seventh Edition (2003) "Myoblast".

Parekkadan, Biju, B.S., et al.; "Osmotic Selection of Human Mesenchymal Stem/Progenitor Cells From Umbilical Cord Blood;" Tissue Engineering, vol. 13, pp. 2465-2473; Nov. 10, 2007.

Huber, Irit et al.; "Identification and Selection of Cardiomyocytes During Human Embryonic Stem Cell Differentiation;" The FASEB Journal, Research Communication; pp. 2551-2563; Mar. 1, 2007.

Wu, Xu et al.; "Small Molecules That Induce Cardiomyogenesis in Embryonic Stem Cells;" JACS Communications; vol. 126, No. 6; pp. 1590-1591; Oct. 8, 2003.

Hirata, Hirokazu et al.; "Coexpression of Platelet-Derived Growth Factor Receptor Alpha and Fetal Liver Kinase 1 Enhances Cardiogenic Potential in Embryonic Stem Cell Differentiation in Vitro;" Journal of Bioscience and Bioengineering; vol. 103, No. 5; pp. 412-419; Feb. 6, 2007.

Muller, M., et al.; "Selection of Ventricular-Like Cardiomyocytes From ES Cells in Vitro;" The FASEB Journal; vol. 14; pp. 2540-2548; Dec. 2000.

Schroder, Astrid R.W. et al.; "HIV-1 Integration in the Human Genome Favors Active Genes and Local Hotspots;" Cell, vol. 110, pp. 521-529; Aug. 23, 2002.

Schuldiner, Maya et al.; "Selective Ablation of Human Embryonic Stem Cells Expressing a "Suicide" Gene;" Stem Cells; pp. 257-265; Dec. 2, 2002.

Bieberich, Erhard et al.; "Selective Apoptosis of Pluripotent Mouse and Human Stem Cells by Novel Ceramide Analogues Prevents Teratoma Formation and Enriches for Neural Precursors in ES Cell-Derived Neural Transplants;" JCB:Article; vol. 167; No. 4; pp. 723-734; Nov. 15, 2004.

Choo, Andre B. et al.; "Selection Against Undifferentiated Human Embryonic Stem Cells by a Cytotoxic Antibody Recognizing Podocalyxin-Like Protein-1;" Stem Cells; vol. 26; pp. 1454-1463; Mar. 20, 2008.

Galvez, et al. (2003) *Journal of Biological Chemistry* 278(40): 38484-38494.

* cited by examiner

METHODS FOR INDUCING CELL DEATH IN PLURIPOTENT STEM CELLS AND DIFFERENTIATED CELLS OTHER THAN CARDIAC MYOCYTES

CROSS-REFERENCE TO RELATED APPLICATIONS

This is the U.S. National Stage application of International Patent Application No. PCT/JP2010/056108, filed Mar. 29, 2010, which claims priority to JP 083553/2009, filed Mar. 30, 2009, the disclosures of each of which are hereby incorporated by reference in their entirety.

TECHNICAL FIELD

The present invention relates to a method of inducing cell death in pluripotent stem cells and differentiated cells other than cardiomyocytes derived from pluripotent stem cells such as embryonic stem cells and induced pluripotent stem cells, as a means of purifying cardiomyocytes in the process of inducing the differentiation of cardiomyocytes from pluripotent stem cells.

BACKGROUND ART

Cardiomyocytes in adults have lost proliferating activity and the only way to treat diseases such as severe myocardial infarction and cardiomyopathy is heart transplantation. As of today, however, the shortage of heart donors still stands in the way and there is an urgent need for finding a therapeutic method other than heart transplantation. In contrast, preparing and purifying cardiomyocytes ex vivo and using them as a replacement of cardiomyocytes during treatment of disease is expected to be one of the most promising methods for saving patients with heart disease who have nothing to resort to except heart transplantation.

Cardiomyocytes are known to be obtainable by various methods including differentiation of stem cells (e.g. embryonic stem cells and a variety of adult stem cells) and acquisition from embryos. Depending on the pluripotent stem cell to be used, a suitable differentiation inhibiting factor (e.g. feeder cell or a leukemia inhibiting factor (LIF) in the case of using mouse pluripotent stem cells, or feeder cell, a basic fibroblast growth factor (bFGF) or a transforming growth factor (TGF) in the case of using human pluripotent stem cells) is removed from a culture medium to thereby induce formation of cell masses (embryoid bodies) and this is known as a method that can initiate differentiation of stem cells into cardiomyocytes.

The mode of ex vivo differentiation of stem cells into cardiomyocytes mimics some of the stages of in vivo physiological development and especially concerning events during early development, the modes of physiological development that takes place in fertilized egg cells and in vitro differentiation have a lot in common. The chronology of ex vivo differentiation into cardiomyocytes is the same as that of physiological development, starting with a differentiation of stem cells into undifferentiated mesodermal cells, some of which differentiate into programmed cardiomyocytes (pre-cardiac mesoderm) which in turn differentiate into cardiomyocytes.

Since pluripotent cells are cells that have the ability to differentiate into all cells that constitute an organ, it is technically difficult to differentiate them into cardiomyocytes only. It is also very difficult to ensure that all pluripotent stem cells are simultaneously induced to the differentiation stage, so it is quite common that stem cells remain undifferentiated in embryoid bodies.

Thus, an attempt to induce the differentiation of stem cells into cardiomyocytes ex vivo involves a problem deleterious to clinical application in that any types of stem cells can result in producing cells other than cardiomyocytes as a by-product or that some cells might remain undifferentiated. Especially, the residual undifferentiated cells have proliferating activity and are capable of differentiating into a great variety of cells, so if cells transplanted into the living body used in the therapy contain any residual undifferentiated cells, the likelihood that teratoma is formed from such undifferentiated cells is extremely high. For this reason, a cell population containing cardiomyocytes prepared by inducing the differentiation of pluripotent stem cells might be directly transplanted into the living body for treatment without great difficulty. Therefore, in order to ensure that a treatment using cardiomyocytes derived from pluripotent stem cells is performed with safety to secure an ideal therapeutic effect, it is necessary to find a method by which undifferentiated pluripotent stem cells are completely excluded and cardiomyocytes are highly purified (namely, a method for removing cells other than cardiomyocytes).

A currently known method for purifying cardiomyocytes is by preliminarily introducing a certain marker gene (e.g. GFP) into the genome of a stem cell (Non-Patent Document 1). However, this method requires genomic alteration, which itself presents an aesthetic problem and it also involves unpredictable serious risks in safety, such as a change in cell's canceration rate (Non-Patent Document 2). A method involving genomic alteration has also been reported as a way to positively remove undifferentiated pluripotent stem cells (Non-Patent Document 3). A method taking a different approach has been reported, in which ceramide analogues known to have a cell death inducing action are used to induce cell death in embryonic stem cells in a comparatively specific way (Non-Patent Document 4). However, this method does not assure satisfactory removal of pluripotent stem cells since the group of cells cultured after treatment with the ceramide analogues contained (OCT positive cells) in an amount as much as a third of those found in the untreated cell group (control). And as regards the removal of human embryonic stem cells, Non-Patent Document 4 only mentions that cells undergoing apoptosis were found and it does not say that satisfactory removal of pluripotent stem cells was effected. A method of using cytotoxic antibodies has been reported (Non-Patent Document 5) but the document states that, even after the treatment with the antibodies by this method, approximately 20% of embryonic stem cells still remained to be removed. As a further problem, utilization of the method involves several constraints such as the need to avoid the antigenicity of the antibodies before they can be used for therapeutic treatment. Thus, the known methods for inducing cell death have a room for improvement as a way to purify cardiomyocytes that can be used in the treatment of myocardial diseases, so it is desired to develop a new and even more efficient method for inducing cell death.

CITATION LIST

Non-Patent Literature

Non-Patent Document 1: Müller, M. et al., FASEB J. 2000; 14: 2540-2548

Non-Patent Document 2: Schröder, A. R. et al., Cell 2002; 110: 521-529

Non-Patent Document 3: Schuldiner, M. et al., Stem Cells 2003; 21: 257-265
Non-Patent Document 4: Bieberich, E. et al., J. Cell Biol. 2004; 167: 723-734
Non-Patent Document 5: CHOO, A. B. et al., Stem Cells 2008; 26: 1454-1463

SUMMARY OF INVENTION

Technical Problems

An object of the present invention is to develop a method that does not involve genomic modification and which yet is capable of inducing cell death in pluripotent stem cells such as embryonic stem cells and induced pluripotent stem cells, as well as in differentiated cells other than cardiomyocytes derived from pluripotent stem cells, but not in cardiomyocytes. It is also an object of the present invention to develop a process for preparing safe and high-purity cardiomyocytes which are free from the risk of teratomas from pluripotent stem cells according to this method.

Solution to Problems

As a result of the intensive studies conducted to solve the aforementioned problems, the present inventors have revealed that by establishing a method capable of inducing cell death in differentiated cells other than cardiomyocytes in a short period of time and in a very efficient manner by adding a substance having no recognized inherent toxicity or cell death inducing action to the culture conditions for pluripotent stem cells and non-cardiomyocytes, the stated problems can be solved without relying upon genomic modification. This method also ensures efficient purification of cardiomyocytes since it does not induce cell death in cardiomyocytes.

Specifically, the present invention provides a method which comprises culturing a cell population including pluripotent stem cells, differentiated cells other than cardiomyocytes derived from pluripotent stem cells, and pluripotent stem cell-derived cardiomyocytes in a hypertonic solution having an osmotic pressure of 370 mOsm/kg or higher, whereby the pluripotent stem cells and differentiated cells other than cardiomyocytes derived from pluripotent stem cells are brought to cell death, and it has become clear that the above-mentioned problems can be solved by providing this method. Thus, the present invention specifically concerns the following.

(1) A method for inducing cell death in pluripotent stem cells and cells other than cardiomyocytes derived from pluripotent stem cells by culturing a cell population including pluripotent stem cells, cells other than cardiomyocytes derived from pluripotent stem cells, and pluripotent stem cell-derived cardiomyocytes in a hypertonic solution having an osmotic pressure of 370 mOsm/kg or higher.
(2) The method recited in (1) above, wherein the culture is conducted in the hypertonic solution for 2 hours or longer.
(3) The method recited in (1) or (2) above, wherein the hypertonic solution having an osmotic pressure of 370 mOsm/kg or higher is prepared by adding saccharides (carbohydrates) to a culture medium.
(4) The method recited in (3) above, wherein the hypertonic solution having an osmotic pressure of 370 mOsm/kg or higher contains 0.1-1M of saccharides.
(5) The method recited in (3) or (4) above, wherein the saccharides are sugar alcohols, sugars, or betaines.

(6) The method recited in (5) above, wherein the sugar alcohols, sugars, or betaines are selected from the group consisting of mannitol, sorbitol, xylitol, glycerol, sucrose, glucose, and trimethylglycine.
(7) The method recited in (4) above, wherein the hypertonic solution having an osmotic pressure of 370 mOsm/kg or higher contains 0.1-0.6 M glycerol.
(8) The method recited in (7) above, wherein the culture is conducted for 10 hours or longer.
(9) The method recited in any one of (1) to (8) above, wherein the cell population, after being cultured in the hypertonic solution, is returned to a culture medium having the normal osmotic pressure of 200-300 mOsm/kg and subjected to further culture.

Advantageous Effect of Invention

When the cell population including pluripotent stem cells, differentiated cells other than cardiomyocytes derived from pluripotent stem cells, and pluripotent stem cell-derived cardiomyocytes is treated by the method of the present invention, any undifferentiated pluripotent stem cells and non-cardiomyocytes in the cell population are efficiently removed while permitting selective survival of cardiomyocytes; hence, the method of the present invention assures efficient enrichment and purification of cardiomyocytes.

BRIEF DESCRIPTION OF DRAWINGS

The patent or application file contains at least one drawing executed in color. Copies of this patent or patent application publication with color drawing(s) will be provided by the U.S. Patent and Trademark Office upon request and payment of the necessary fee.

DESCRIPTION OF EMBODIMENTS

Figure 1:
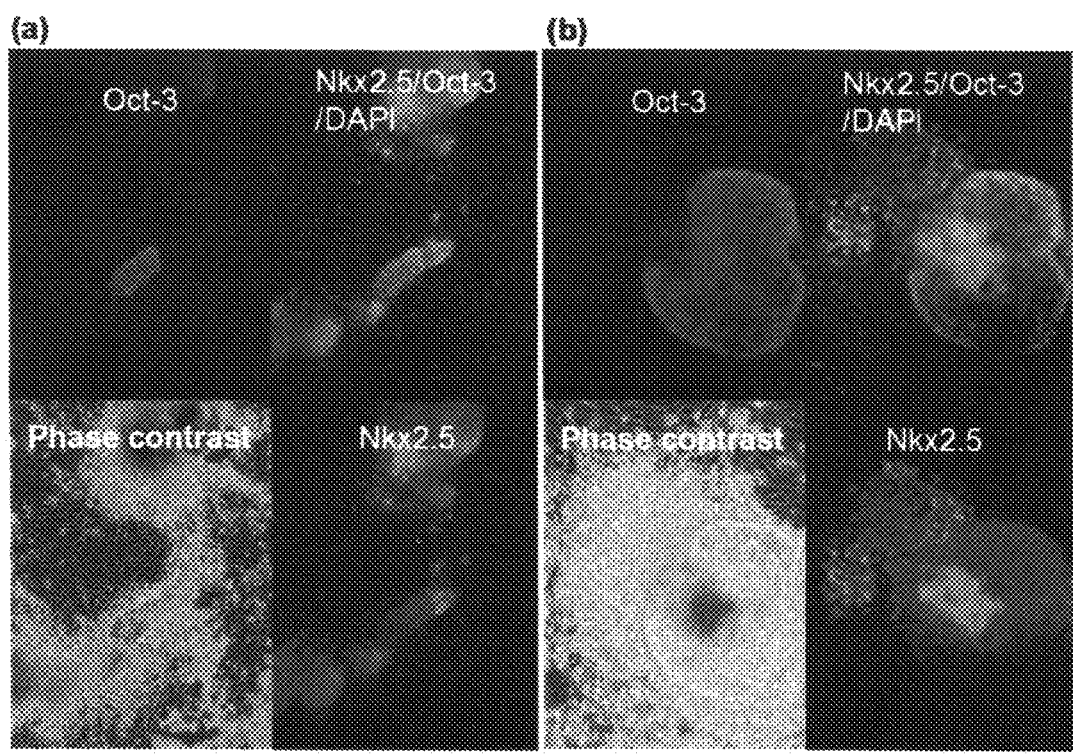
FIG. 1 shows the results of immunostaining of embryonic stem cell-(ES cell-) derived cardiomyocytes and residual undifferentiated embryonic stem cells.

The present inventors prepared hypertonic solutions containing mannitol dissolved in it at high concentrations and applied those hypertonic solutions to a mixed cell system comprising embryonic stem cells as well as cardiomyocytes and non-cardiomyocytes; they found the fact that upon exposure to the hypertonic solutions, the embryonic stem cells and non-cardiomyocytes were more likely to undergo cell death. Given this finding, the present inventors conducted a closer study on how the mannitol concentration and the duration of exposure to mannitol would relate to the cell death of embryonic stem cells and non-cardiomyocytes; as a result, the present inventors found that prolonged exposure to low concentrations of mannitol effectively induced cell death in embryonic stem cells and non-cardiomyocytes and that at 1M which was a substantially saturated concentration, mannitol induced cell death in embryonic stem cells within a short period of time.

At the same time, the present inventors found that over the entire concentration range of mannitol, there were concentration and time conditions that would cause cell death in embryonic stem cells and non-cardiomyocytes but which yet would not induce cell death in cardiomyocytes differentiated from the embryonic stem cells. Hence, the method of the present invention which performs culture under such conditions not only achieves efficient removal of embryonic stem cells and non-cardiomyocytes but also assures efficient enrichment and purification of cardiomyocytes.

Hence, in one embodiment of the present invention, there is provided a method for inducing cell death in pluripotent stem cells and differentiated cells other than cardiomyocytes derived from pluripotent stem cells by culturing a cell population including pluripotent stem cells, differentiated cells other than cardiomyocytes derived from pluripotent stem cells, and pluripotent stem cell-derived cardiomyocytes in a hypertonic solution having an osmotic pressure of 370 mOsm/kg or higher.

When mouse embryonic stem cells are induced to differentiate by the embryoid body forming method, embryoid bodies at 3-6 days after the start of induction for differentiation are said to include mesoderms or programmed cardiomyocytes. Cardiomyocytes appear at 7 days after the start of differentiation (10 days for human embryonic stem cells). The embryoid bodies also include undifferentiated cells, endothelial epithelium-like cells, and neuronal cells. Upon closer study of the cells that constitute the embryoid bodies, 70-80% of the cell populations that compose them are occupied by differentiated cells other than cardiomyocytes, occasionally by undifferentiated embryonic stem cells. These contaminating cells proliferate actively and their relative abundance increases with the course of time. The present inventors found that when embryoid bodies having such cell composition were exposed to an appropriate range of high osmotic pressure in a culture medium, the residual embryonic stem cells and differentiated cells other than cardiomyocytes in the embryoid bodies underwent cell death. The present inventors also found that even under these culture conditions, cardiomyocytes did not undergo cell death and resumed autonomous pulsation when the culture medium was replaced by one having the physiological osmotic pressure.

In the method of the present invention, the source of cell supply may be a cell population derived from any supply source as long as it contains cardiomyocytes. For example, the method of the present invention can be implemented by using a cell population including cardiomyocytes differentiated from pluripotent stem cells (including embryonic stem cells (ES cells), adult stem cells, induced pluripotent stem cells (iPS cells), etc.) under known conditions for inducing cardiomyocytes, or by using a cell population derived from embryonic tissue. Aside from the pluripotent stem cell-derived cardiomyocytes, the cell population containing cardiomyocytes thus differentiated from pluripotent stem cells may contain pluripotent stem cells and differentiated cells other than the cardiomyocytes derived from pluripotent stem cells.

The method of the present invention is characterized by culturing the above-defined cell population with a hypertonic solution having an osmotic pressure of 370 mOsm/kg or higher. The osmotic pressure used in the method of the present invention is one that induces cell death in cells other than cardiomyocytes (i.e., pluripotent stem cells and differentiated cells other than cardiomyocytes) but not in cardiomyocytes. The osmotic pressure that satisfies this requirement is 370 mOsm/kg or higher, preferably 370 mOsm/kg-1600 mOsm/kg, more preferably 370 mOsm/kg-1000 mOsm/kg, even more preferably 480 mOsm/kg-1000 mOsm/kg, and most preferably 700 mOsm/kg-1000 mOsm/kg. Considering that the osmotic pressure under in vitro culture conditions is usually about 200-300 mOsm/kg (also called the normal or physiological osmotic pressure), those values are extraordinarily high and if cultured under this condition, all cells other than cardiomyocytes will undergo cell death.

In the case where the hypertonic solution having an osmotic pressure of 370 mOsm/kg or higher as prepared by adding a saccharide to a culture medium is used, the method of the present invention is characterized by performing culture in such hypertonic solution for 2 hours or longer, preferably for 2-72 hours, more preferably for 2-48 hours, even more preferably for 2-24 hours, and most preferably for 4-12 hours.

In the method of the present invention, the condition that can selectively induce cell death in undifferentiated pluripotent stem cells including human ES cells and iPS cells, or differentiated cells other than cardiomyocytes is determined by the relation between the degree of the osmotic pressure exerted by the hypertonic solution and the length of time over which cells are exposed to the hypertonic solution. Briefly, regardless of the cell species to be used to induce cardiomyocytes, the higher the osmotic pressure of the hypertonic solution, the shorter the time the cells need be exposed to it, and the lower the value at which the osmotic pressure of the hypertonic solution is set, the longer the time for which the cells must be exposed to the hypertonic solution.

When the cell population is exposed to the hypertonic solution in the method of the present invention, cells other than cardiomyocytes (undifferentiated pluripotent stem cells or non-cardiomyocytes) can be brought to cell death (namely, cell death is induced or a signal for cell death is given). The cells thus brought to cell death either undergo cell death in the hypertonic solution or undergo cell death after they are recovered from the hypertonic solution and put back into a normal culture medium.

In the method of the present invention, cell death is induced by exposing the cells to a physiological stress, so cell death can be selectively induced in the cells other than the desired ones without causing any genetic damage to the surviving cells; in this respect, the present invention is quite preferred over inducing cell death by means of a physical condition (e.g. radiation stress or oxidation stress) or a chemical condition (compound stress) that will cause direct damage to genes. To be more specific, the cells that have survived the physiological stress will restore their initial function and can exhibit the normal function if they are reverted to culture conditions that are free from the physiological stress applied for inducing cell death. This feature is one that is quite easy to utilize in settings of regenerative medicine which involves preparing a tissue or tissue-constituting cells ex vivo and transplanting them into the living body.

The term "hypertonic solution having an osmotic pressure of 370 mOsm/kg or higher" as used herein means a hypertonic solution that is adjusted solely in terms of osmotic pressure to 370 mOsm/kg or higher without affecting the metabolism of cells, and it may be exemplified by one that is prepared by adding a saccharide (carbohydrate) to a culture medium. The saccharide that can be used in the present invention may be exemplified by ones that are capable of increasing the osmotic pressure of the culture medium without affecting the metabolism of cells; specific examples include, but are not limited to, saccharides (monosaccharides, oligosaccharides, and polysaccharides), glycosaminoglycans, aminoglycosides, sugar alcohols, and betaines. More specific examples are the substances that are listed in Table 1.

TABLE 1

| Saccharides (carbohydrates) | | |
|---|---|---|
| Classification (large) | Classification (small) | Exemplary constituents |
| Mono-saccharides | Triose | ketotriose (dihydroxyacetone), aldotriose (glyceraldehyde) |
| | Tetrose | ketotetrose (erythrulose), aldotetrose (erythrose, threose) |
| | Pentose | ketopentose (ribulose, xylulose) |
| | | aldopentose (ribose, arabinose, xylose, lyxose) |
| | | deoxysaccharide (deoxyribose) |
| | Hexose | ketohexose (psicose, fructose, sorbose, tagatose) |
| | | aldohexose (allose, altrose, glucose, mannose, gulose, idose, galactose, talose) |
| | | deoxysaccharide (fucose, fuculose, rhamnose) |
| | Heptose | sedoheptulose |
| Oligo-saccharides | Di-saccharide | sucrose, lactose, maltose, trehalose, turanose, cellobiose |
| | Tri-saccharide | raffinose, melezitose, maltotriose |
| | Tetra-saccharide | acarbose, stachyose |
| | Other oligo-saccharides | fructooligosaccharide (FOS), galactooligosaccharide (GOS), mannanoligosaccharide (MOS) |
| Poly-saccharides | Poly-saccharide | glycogen, starch (amylose, amylopectin), cellulose, dextrin, glucan ($\beta$1,3-glucan) |
| | | fructose: fructans (inulin, levan ($\beta$2→6)) |
| | | N-acetylglucosamine: chitin |
| Glycosaminoglycans | | heparin, chondroitin sulfrate, hyaluronan, heparan sulfate, dermatan sulfate, keratan sulfate |
| Aminoglyco-sides | | kanamycin, streptomycin, tobramycin, neomycin, paromomycin, apramycin, gentamicin, netilmicin, amikacin |
| Sugar alcohols | | erythritol, glycerol, isomaltolactitol, maltitol, mannitol, sorbitol, xylitol, D-threitol, L-threitol, D-arabinitol, L- arabinitol, ribitol (adonitol), D-iditol, galactitol (dulcitol), volemitol, perseitol, D-erythro-D-galacto-octitol, inositol |
| Betaines | | carnitine, trimethylglycine (betaine) |

The effect of the present invention was also recognized in the case of using sorbitol (an example of sugar alcohols), trimethylglycine (an example of betaines), and other substances that are involved physiologically in the regulation of osmotic pressure in the living body; hence, betaine, taurine, inositol, glycerophosphocholine, etc. can be used as organic osmolytes.

When the hypertonic solution having an osmotic pressure of 370 mOsm/kg or higher is prepared by adding a saccharide to the culture medium, the method of the present invention is characterized in that the hypertonic solution contains the saccharide in 0.1-1 M (mol/L), preferably 0.1-0.6 M (mol/L). The relation between the concentration of saccharide (mol/L) and the osmotic pressure (mOsm/kg) can be approximated by a substantially straight line; a hypertonic solution containing 0.1 M saccharide corresponds to one having an osmotic pressure of approximately 370 mOsm/kg and a hypertonic solution containing 1 M saccharide corresponds to one having an osmotic pressure of approximately 1300-1600 mOsm/kg.

If glycerol is used as the saccharide, the method of the present invention is characterized in that the hypertonic solution contains 0.1-0.6 M glycerol, preferably 0.1-0.5 M glycerol, and it may be further characterized by performing culture in this hypertonic solution for 10 hours of more, typically for 10-24 hours, preferably for 10-18 hours.

Hypertonic solutions were prepared using various saccharides and the relation between the saccharide concentration and the osmotic pressure is shown in the following table for typical saccharides.

TABLE 2

Saccharide Concentration and Osmotic Pressure (Measured values)

| Concentration (M) | 0 | 0.45 | 0.6 | 0.9 |
|---|---|---|---|---|
| Glycerol | 258 | 706 | 869 | 1232 |
| Glucose | 258 | 758 | 939 | 1336 |
| Mannitol | 258 | 717 | 875 | 1234 |
| Sucrose | 258 | 779 | 988 | 1496 |
| Xylitol | 258 | 779 | 940 | 1230 |
| Sorbitol | 258 | 748 | 922 | 1289 |
| Betaine | 258 | 763 | 965 | 1421 |

In the method of the present invention, after the cell population is cultured in the hypertonic solution having an osmotic pressure of 370 mOsm/kg or higher to induce cell death in pluripotent stem cells and non-cardiomyocytes, it is preferably reverted to a culture medium having the normal osmotic pressure (i.e., an osmotic pressure of 200-300 mOsm/kg) and subjected to further culture. When the cell population is cultured in the hypertonic solution used in the method of the present invention, cardiomyocytes will not undergo cell death but they might experience a transient arrest of pulsation. Even in this case, if the cell population is reverted into a culture medium having the normal osmotic pressure, the cardiomyocytes will resume pulsation to function normally. As a further problem, the cell population cultured in the hypertonic solution also contains cells that have received a signal for cell death but which appear still alive. To remove these cells from the cultured cell population, it is preferred that the cell population is reverted into a culture medium having the normal osmotic pressure and subjected to further culture.

The method of the present invention could exhibit the same results in all kinds of cells that were tested in the Examples that follow (i.e., mouse-derived embryonic stem cells, marmoset-derived embryonic stem cells, human-derived embryonic stem cells, and human-derived iPS cells). Since the method of the present invention was not dependent on the animal species, it was shown that the method of the present invention is applicable to the cells derived from all mammals ranging from mouse to human. Furthermore, the method of the present invention could solve the intended problem in both embryonic stem cells and induced pluripotent stem cells, so it was shown that the method of the present invention is applicable irrespective of whether the pluripotent stem cells are ones that have not been subjected to gene manipulation (e.g. embryonic stem cells) or ones that have been subjected to gene manipulation (e.g. iPS cells).

Described below is a specific way to apply the method of the present invention to a cell population containing cardiomyocytes derived from embryonic stem cells or iPS cells. First, embryonic stem cells or iPS cells are subjected to suspension culture by the hanging-drop method or the like in a differentiating culture medium (comprising, for example, α-MEM (minimum essential medium) (SIGMA) supplemented with 10% FBS (EQUITEC BIO), 100 units/ml penicillin, and 50 μg/ml streptomycin (GIBCO)), whereby appropriate induction for differentiation into cardiomyocytes was performed to form embryoid bodies containing cardiomyocytes. After the differentiation into cardiomyocytes, maturation was effected for an additional period of at least 2 days; subsequently, the culture medium was replaced by one suitable for culturing the embryoid bodies, i.e., a serum-free α-MEM or D-MEM culture medium containing 0.1-1 M mannitol, sorbitol, glucose, sucrose or xylitol (this culture medium is the hypertonic solution) and the embryoid bodies were exposed to the new culture medium (hypertonic solution) for an additional specified period of time. This exposure to the hypertonic solution was capable of inducing cell death in or conferring a signal for cell death to cells other than cardiomyocytes (undifferentiated pluripotent stem cells or non-cardiomyocytes).

When the culture involving exposure to the hypertonic solution ends, the culture medium is replaced by one having the normal osmotic pressure and the treated cells are subjected to continued culture for an additional period, whereby the cardiomyocytes can selectively be allowed to survive under the culture conditions. If necessary, the cells may be washed by enzymatic dispersion, culture medium replacement, centrifugation or any other suitable techniques, which are used either independently or in combination, to thereby ensure that the non-cardiomyocytes undergoing cell death are removed positively.

If the cell population comprising both cardiomyocytes and cells other than cardiomyocytes that include undifferentiated cells is exposed to the hypertonic solution by the method of the present invention, cell death can be induced in at least 90%, preferably at least 95%, more preferably at least 98%, and most preferably at least 100%, of the cells other than cardiomyocytes that are contained in the cell population.

EXAMPLES

The present invention is described in greater detail by means of the following Examples. It should, however, be noted that the following Examples serve to illustrate the present invention and are by no means intended to limit the same.

Example 1

Immunostaining of Embryonic Stem Cell-Derived Cardiomyocytes and Residual Undifferentiated Embryonic Stem Cells In this Example, cell masses (embryoid bodies) containing cardiomyocytes were formed from stem cells and checked for the presence of both cardiomyocytes and undifferentiated cells in them.

Mouse embryonic stem cells (cell line: EB3, Nat Genet. 2000; 24: 372-376) were provided by courtesy of Dr. Hitoshi Niwa at RIKEN. These mouse embryonic stem cells were differentiated into cell masses containing cardiomyocytes by a known method (Bader, A. et al., Differentiation 2001, 68, pp. 31-43); viz., culturing 75 embryonic stem cells per an embrioid body (EB) as cell masses for a total of 7 days by the hanging-drop technique using a culture medium [α-MEM (minimum essential medium) (SIGMA), supplemented with 10% FBS (EQUITEC BIO), 100 units/ml penicillin, and 50 μg/ml streptomycin (GIBCO)]); thereafter, the embryoid bodies were adhered to the culture dish and cultured for another 3-5 days under the conditions of 37° C. and 5% $CO_2$.

Thus obtained embryoid bodies were fixed with 4% paraformaldehyde and further treated with 0.1% Triton X100 to render the cell membrane semi-soluble. After blocking with a 4% BSA solution, an antibody against Nkx 2.5 (goat anti-Nkx 2.5 antibody; No. N-19 of Santacruz) generally held to appear in programmed cardiomyocytes at the earliest stage of development and an antibody against the transcription factor Oct-3/4 (mouse anti-Oct-3/4 monoclonal antibody; No. 084720 of BD Transduction Laboratories) generally known to play an important role in maintaining the ability of mouse embryonic stem cells to remain undifferentiated, both being used as primary antibodies, were diluted 100 folds with a block solution and allowed to permeate at 4° C. for 12 hours. After washing four times, Alexa Flow 488 labeled donkey anti-goat antibody (Molecular Probe) and TRITC labeled rabbit anti-mouse antibody (DAKO), selected as the secondary antibodies for the respective primary ones, were both diluted 1/200 and allowed to permeate at room temperature for 1 hour. After washing, nuclear staining was performed at room temperature for 5 minutes using a solution containing the nuclear DNA staining reagent DAPI (Molecular Probe). After washing, observation was made under a fluorescent microscope. The results are shown in FIG. 1. For two embryoid bodies ((a) and (b) in FIG. 1), the top left panel refers to Oct-3 (red), the bottom right panel refers to Nkx 2.5 (green), the top right panel shows a merged image of Oct-3 (red) and Nkx 2.5 (green), with DAPI stain (blue) further merged on it, and the bottom left panel shows a phase contrast image.

As FIG. 1 shows, it was found that each of embryoid bodies (a) and (b) include both Oct-3/4 positive undifferentiated cells and Nkx 2.5 positive cardiomyocytes within a single embryoid body.

Example 2

Treatment with Saccharides (Sugar Alcohols) of Culture System Containing Both Embryonic Stem Cell-Derived Cardiomyocytes and Residual Embryonic Stem Cells In this Example, cell masses (embryoid bodies) containing cardiomyocytes as formed from embryonic stem cells were treated with saccharides (sugar alcohols) and subsequently checked for the state of culture of cardiomyocytes and that of other cells.

Mouse derived embryonic stem cells were treated by the method of Example 1 to form embryoid bodies, which were differentiated to a stage containing the programmed cardiomyocytes (precardiac mesoderms). Thus obtained embryoid bodies were treated with digestive enzymes (trypsin and collagenase) meticulously to ensure that no cell damage would be caused and the resulting partially dispersed embryoid bodies were subjected to another adherent culture. Upon a 5-day continued culture, populations of cardiomyocytes pulsating autonomously (the cell populations circled by the red lines), cell populations having the traits of embryonic stem cells-like cells (the cell populations circled by the yellow lines), and other cell populations were observed together (see FIG. 2(a)).

In the next step, the culture medium for the mixed culture was replaced by a serum-free α-MEM culture medium containing mannitol in 0.45 M (approximately equivalent to 720 mOsm/kg) and ITS {insulin (10 mg/L), transferrin (5.5 mg/L), and sodium selenite (6.7 mg/L)} (GIBCO) and culture was performed for 36 hours. As it turned out, a great number of cells had already showed typical signs of typical cell death at that stage. Subsequently, the culture medium was replaced by an α-MEM culture medium supplemented with 20% fetal calf serum and culture was continued, whereupon the cardiomyocytes restored autonomous pulsation in 1 or 2 days. In contrast, virtually all cells other than cardiomyocytes were found dead (see FIG. 2(b)), including the undifferentiated cells (embryonic stem cells) which spread on the culture dish in such a way as to form a monolayer (see the bottom right panel of FIG. 2(a).)

Figure 2:
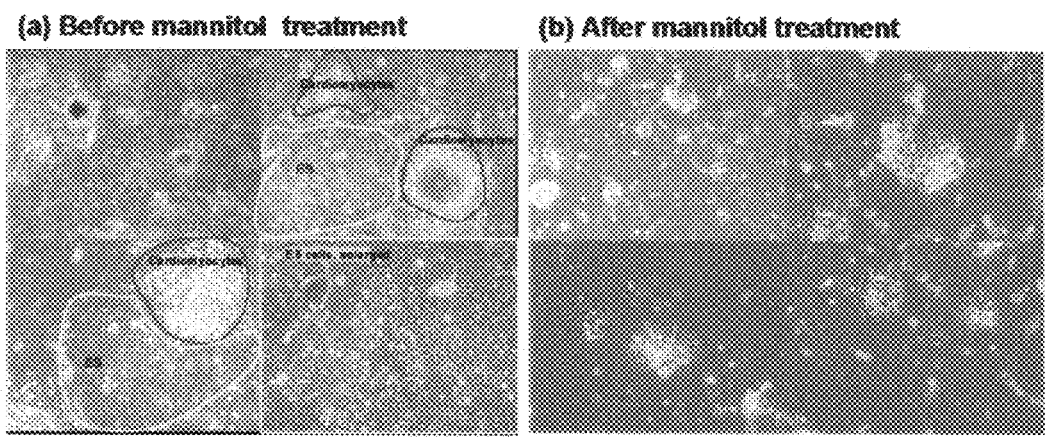
FIG. 2 shows the results of treatment with mannitol of a culture system comprising both embryonic stem cell-derived cardiomyocytes and residual undifferentiated embryonic stem cells.
Figure 3:
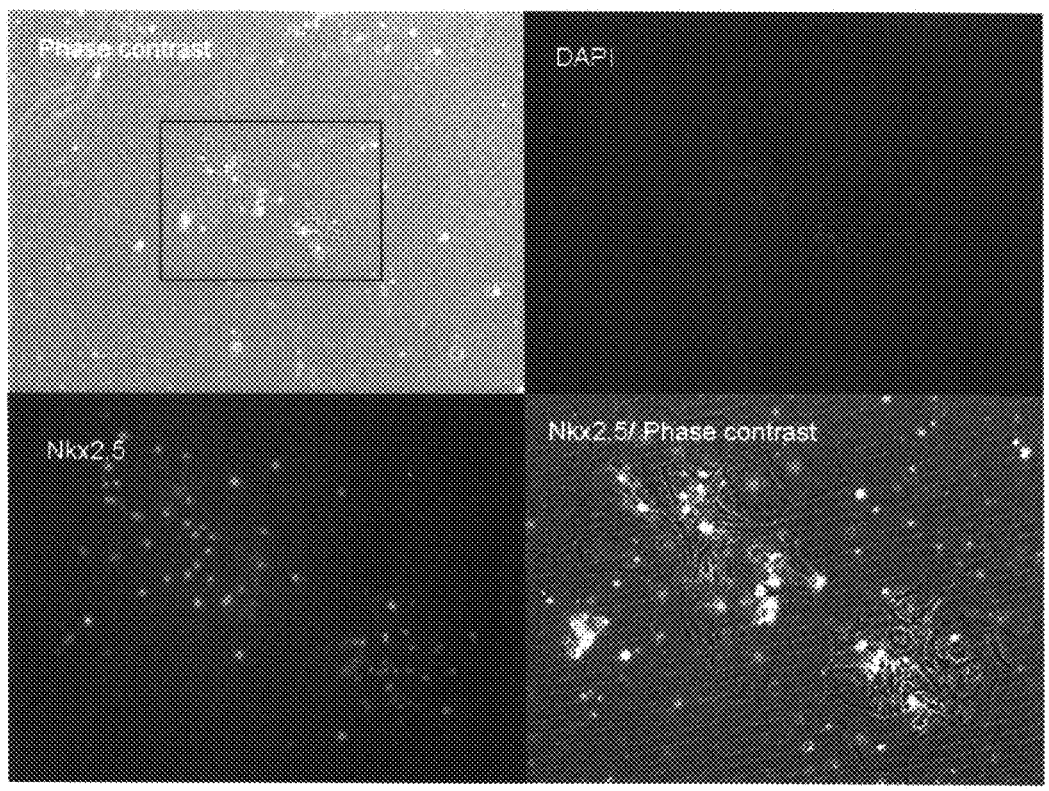
FIG. 3 shows the results of immunostaining with an antibody against Nkx 2.5 and that against Oct-3/4 in cells after treatment with mannitol.

The culture depicted in FIG. 2 was subjected to immunostaining with antibodies against Nkx 2.5 and Oct-3/4 by the same method as used in Example 1 and the results are shown in FIG. 3. For the cells bounded by the rectangle in the phase contrast image depicted in the top left panel of FIG. 3, the bottom left panel shows staining with the antibody against Nkx 2.5 (green), the top right panel shows DAPI stain (blue), and the bottom right panel shows a merged image of staining with Nkx 2.5 (green) and DAPI stain (blue). As a result, it became clear that 98% and more of the obtained cells were Nxk 2.5 positive cardiomyocytes (see the bottom left and the bottom right panel of FIG. 3), and the Oct-3/4 positive undifferentiated cells were not included in it.

Example 3

Cell Death Inducing Effect of Saccharides (Sugar Alcohols) on Mouse Embryonic Stem Cells In this Example, mouse embryonic stem cells were treated with saccharides (sugar alcohols) and subsequently checked for the state of their survival.

The mitochondrial membrane potential is lost in dead cells, so if cells are stained with the mitochondrial membrane potential sensitive reagent TMRM (Molecular Probe) which emits fluorescence upon detecting the membrane potential which is an indicator of survival, the fluorescence signal derived from this reagent is high in live cells but low in dead cells.

Figure 4:
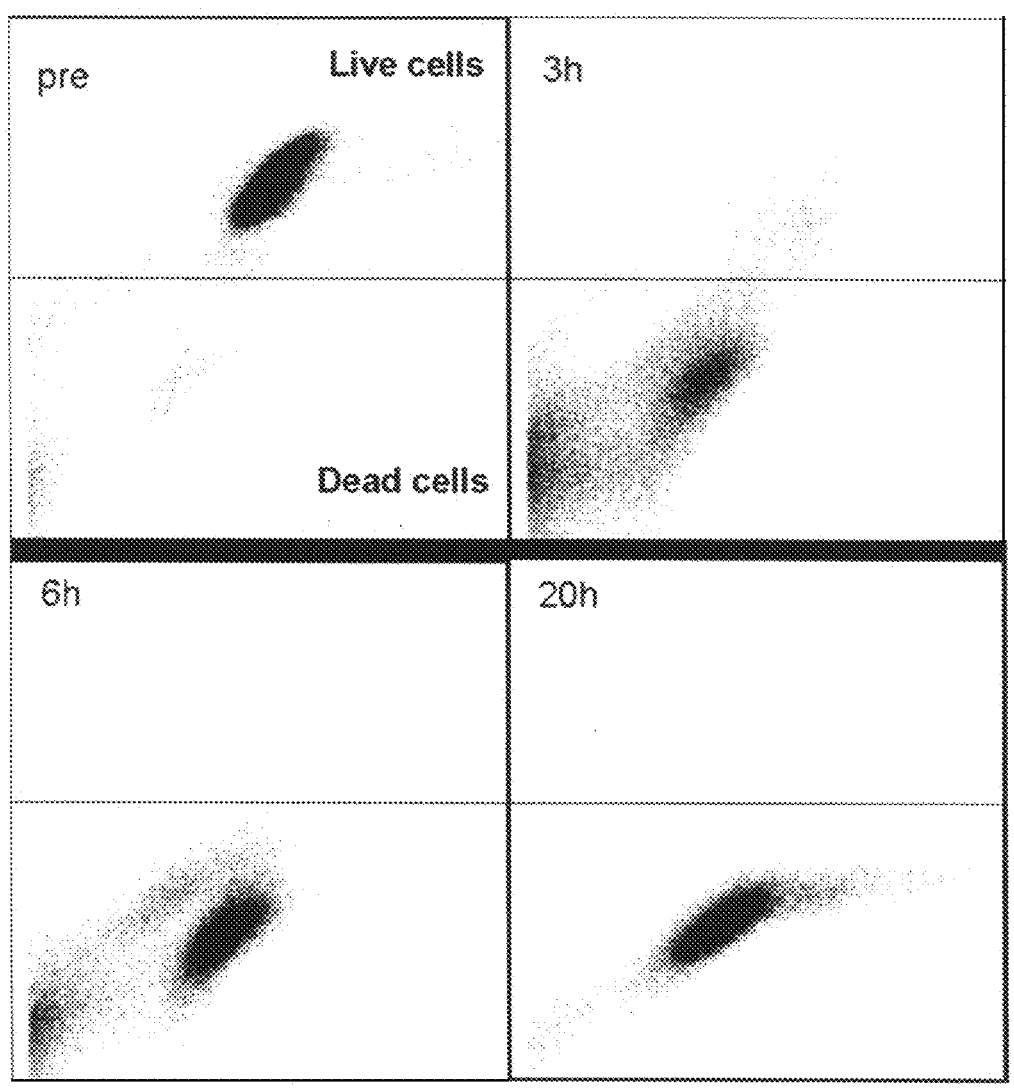
FIG. 4 shows the cell death inducing effect of 0.45 M mannitol on mouse embryonic stem cells.

This feature was used in Example 3; embryonic stem cells cultured by the method of Example 1 were further cultured in an α-MEM culture medium containing 0.45 M mannitol (approximately equivalent to 720 mOsm/kg) and 1 µM TMRM for a period of 0 h (Pre), 3 h, 6 h or 20 h; the cultured embryonic stem cells were harvested, washed and subjected to FACS analysis for checking the state of their survival on the basis of the fluorescence intensity of the mitochondrial membrane potential sensitive reagent TMRM; the results are shown in FIG. 4. In FIG. 4 depicting the results of FACS analysis for 0 h (Pre), 3 h, 6 h, and 20 h, the cells lying above the border line on the dot plots diagrams are live cells and those below the border line are dead cells.

As FIG. 4 shows, virtually all cells were alive before the treatment (Pre) but after the 3-hr treatment with mannitol, approximately 90% of the cells had died and after the 6-hr treatment, 98% of the cells had died; after the 20-hr treatment, all cells had been dead (FIG. 4).

Example 4

Cell Death Inducing Effect of Saccharides (Sugar Alcohols) on Marmoset Embryonic Stem Cells In this Example, marmoset embryonic stem cells were treated with saccharides (sugar alcohols) and subsequently checked for the state of their survival.

The marmoset embryonic stem cells were obtained from the Central Institute for Experimental Animals (Stem Cells, 2005 October; 23(9): 1304-13). The cells were cultured basically in accordance with the method described in this document. To be more specific, the marmoset embryonic stem cells were cultured to maintain their undifferentiated state using mouse embryonic fibroblasts (MEF) that had been inactivated for growth by treatment with mitomycin C. The culture medium of KO-DMEM (GIBCO), supplemented with 20% KO-SERUM (GIBCO), 1.6 mM L-glutamine, 0.1 mM non-essential amino acids (MEM), 0.2 mM β-mercaptoethanol (2-ME; Sigma), 100 IU/ml penicillin, 100 µg/ml streptomycin sulfate, and 8 ng/ml recombinant human leukemia inhibiting factor (LIF; Chemicon) or recombinant human basic fibroblast growth factor (bFGF; Peprotech) was used.

Upon passaging, the cells were treated with 0.1% type III collagenase (Wortington) at 37° C. for 10 minutes to separate ES colonies.

After the passaging, the cells were dispersed with each other using TE (0.25% trypsin (GIBCO) and 1 mM EDTA) and in accordance with a published document (Watanabe, K. et al., Nat. Biotechnol., 2007, 25: 681-686, Epub 2007 May 27), 10 μM of a selective Rho-related kinase (ROCK) inhibitor (Y27632) was added to suppress cell death. At the same time, the mitochondria in the live cells were stained with 50 nM TMRM.

Figure 5:
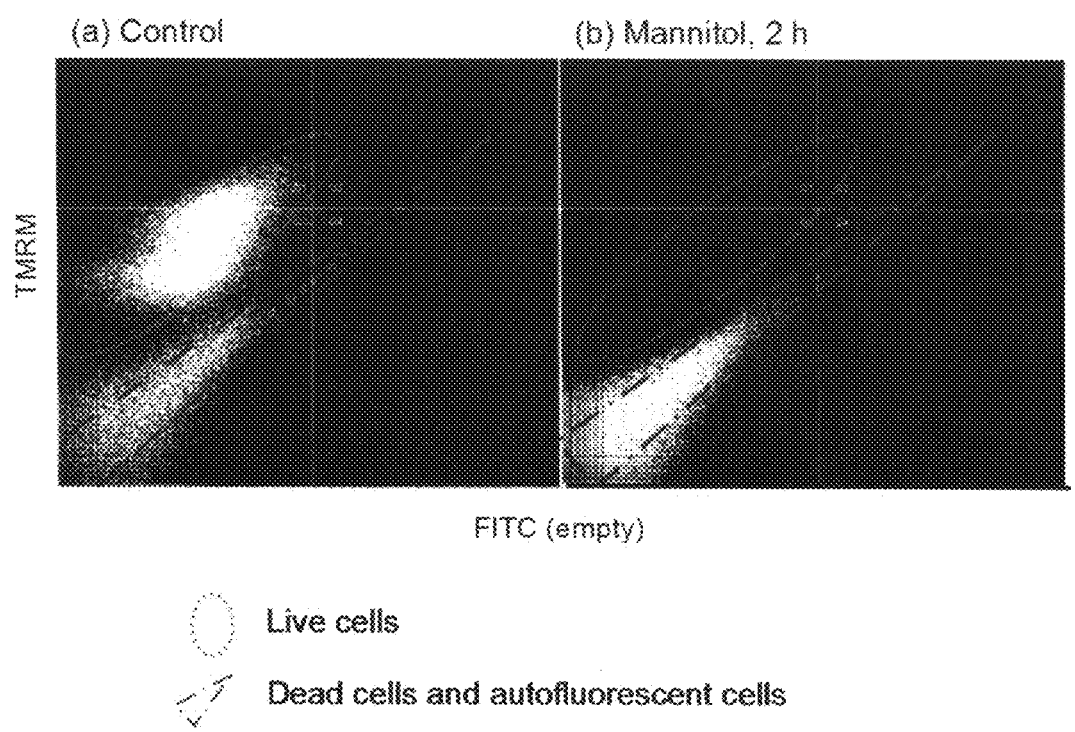
FIG. 5 shows the action of mannitol on marmoset embryonic stem cells, which were determined to be either alive or dead with the mitochondrial membrane potential sensitive dye TMRM.

Part of the stained cells were treated with an α-MEM culture medium containing 0.45 M mannitol (approximately equivalent to 720 mOsm/kg) for 2 hours and a sample was prepared from these cells; the rest of the stained cells were treated with a mannitol-free α-MEM culture medium for 2 hours and a sample was prepared from these cells as a control. In the control, cells were aggregated with each other to make masses, so before FACS analysis, another TE treatment was conducted to disperse the cells. Thereafter, the cells treated with mannitol for 2 hours and the control cells were analyzed by FACS for the level of mitochondrial membrane potential on the basis of the fluorescent intensity of TMRM to check the state of survival of the stem cells; the results are shown in FIG. 5. As is clear from comparison with the control (FIG. 5(a)), almost all of the cells treated with mannitol for 2 hours had lost membrane potential (FIG. 5(b)).

Figure 6:
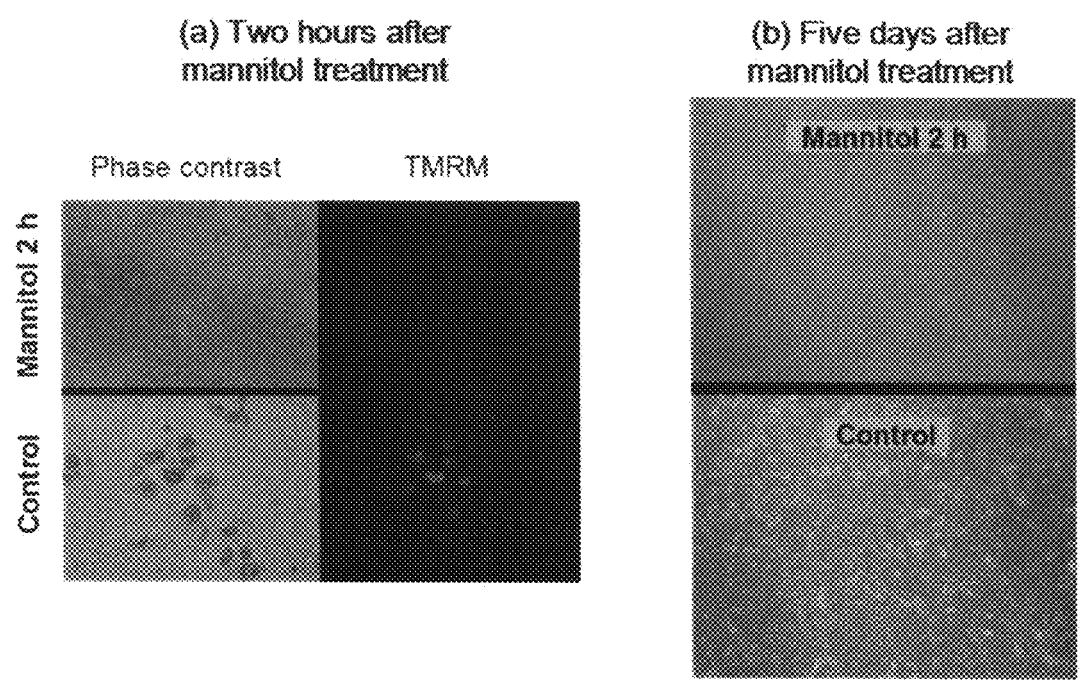
FIG. 6 shows the effect of mannitol on marmoset embryonic stem cells.

In addition, the stained cells were photographed, both for the case of 2-h treatment with mannitol and for the control (FIG. 6(a)). Subsequently, the two types of cells were subjected to adherent culture for 5 days using a culture medium [KO-DMEM (GIBCO), supplemented with 20% KO-SERUM (GIBCO), 1.6 mM L-glutamine, 0.1 mM non-essential amino acids (MEM), 0.2 mM β-mercaptoethanol (2-ME; Sigma), 100 IU/ml penicillin, 100 μg/ml streptomycin sulfate, and 8 ng/ml recombinant human leukemia inhibiting factor (LIF; Chemicon)]; as a result, a large proportion of the control cells (i.e., cells not treated with mannitol) were found alive (the lower panel of FIG. 6(b)) but none of the cells exposed to mannitol were found alive (the upper panel of FIG. 6(b)).

Example 5

Cell Death Inducing Effect of Saccharides (Sugar Alcohols) on Human Embryonic Stem Cells In this Example, human embryonic stem cells were treated with saccharides (sugar alcohols) and subsequently checked for the state of their survival.

The human embryonic stem cells were obtained from Stem Cell Research Center, Institute for Frontier Medical Sciences, Kyoto University (ES cell center sponsored by the National Bio-Resource Project) (Suemori, H et al., Biochem. Biophys. Res. Commun., Vol. 345, 2006, pp. 926-932). The cells were cultured basically in accordance with the method described in this document. To be more specific, the human embryonic stem cells were cultured to maintain their undifferentiated state using mouse embryonic fibroblasts (MEF) that had been inactivated for growth by treatment with mitomycin C. The culture medium of F12/DMEM (1:1) (SIGMA; Product No. D6421), supplemented with 20% KO-SERUM (GIBCO), 1.6 mM L-glutamine, 0.1 mM non-essential amino acids (MEM), 0.1 mM β-mercaptoethanol (2-ME; Sigma), 100 IU/ml penicillin, 100 μg/ml streptomycin sulfate, and recombinant human basic fibroblast growth factor (bFGF; Reprotech) was used. Upon passaging, the cells were treated with 0.1% type III collagenase (Wortington) at 37° C. for 10 minutes to separate embryonic stem cell colonies.

After passaging, the cells were dispersed with each other using TE (0.25% trypsin (GIBCO) and 1 mM EDTA) and in accordance with a published document (Watanabe, K. et al., Nat. Biotechnol., 2007, 25: 681-686, Epub 2007 May 27), 10 μM of a ROCK inhibitor (Y27632) was added to suppress cell death. At the same time, the mitochondria in the live cells were stained with 50 nM TMRM.

Figure 7:
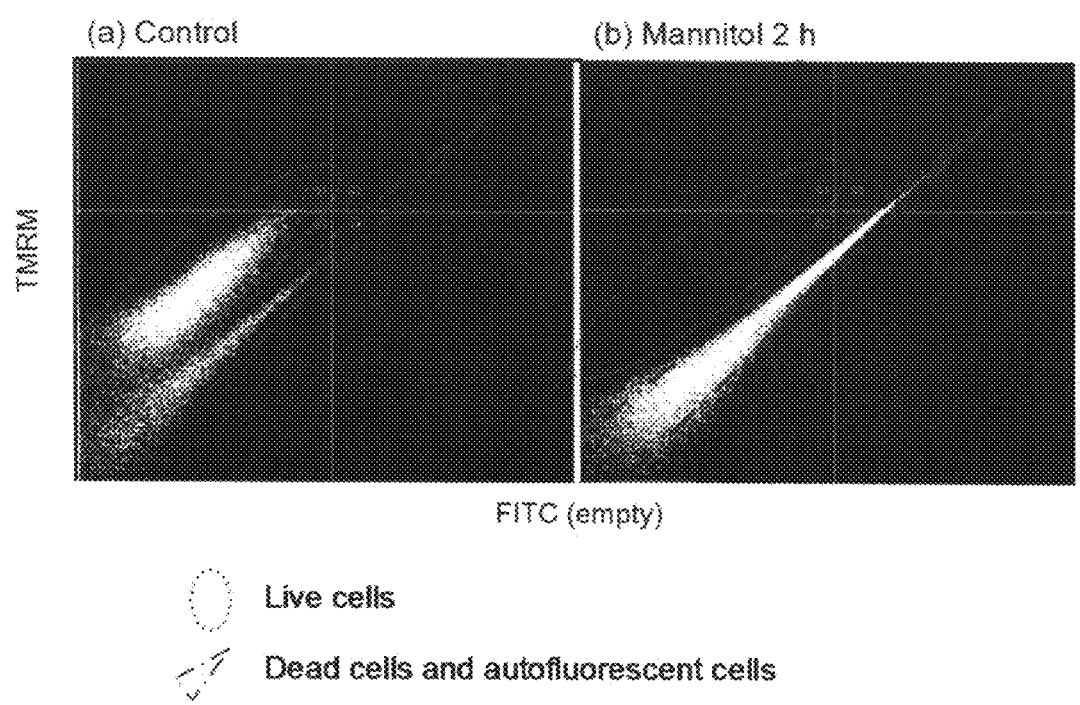
FIG. 7 shows the effect of mannitol on human embryonic stem cells (by FACS analysis).

Part of the stained cells were treated with an α-MEM culture medium containing 0.45 M mannitol (approximately equivalent to 720 mOsm/kg) for 2, 3 or 4 hours and three samples were prepared from these cells; the rest of the stained cells were treated with a mannitol-free α-MEM culture medium for 2 hours and a sample was prepared from these cells as a control. In the control, cells were aggregated with each other to make masses, so before FACS analysis, the treated groups and the control were given another treatment with trypsin and EDTA to disperse the cells. The cells treated with mannitol for 2, 3 or 4 hours and the control cells were analyzed by FACS for the level of mitochondrial membrane potential on the basis of the fluorescent intensity of TMRM to check the state of survival of the stem cells; the results are shown in FIG. 7. As is clear from comparison with the control (FIG. 7(a)), almost all of the cells treated with mannitol for 2 hours had lost membrane potential (FIG. 7(b)).

Figure 8:
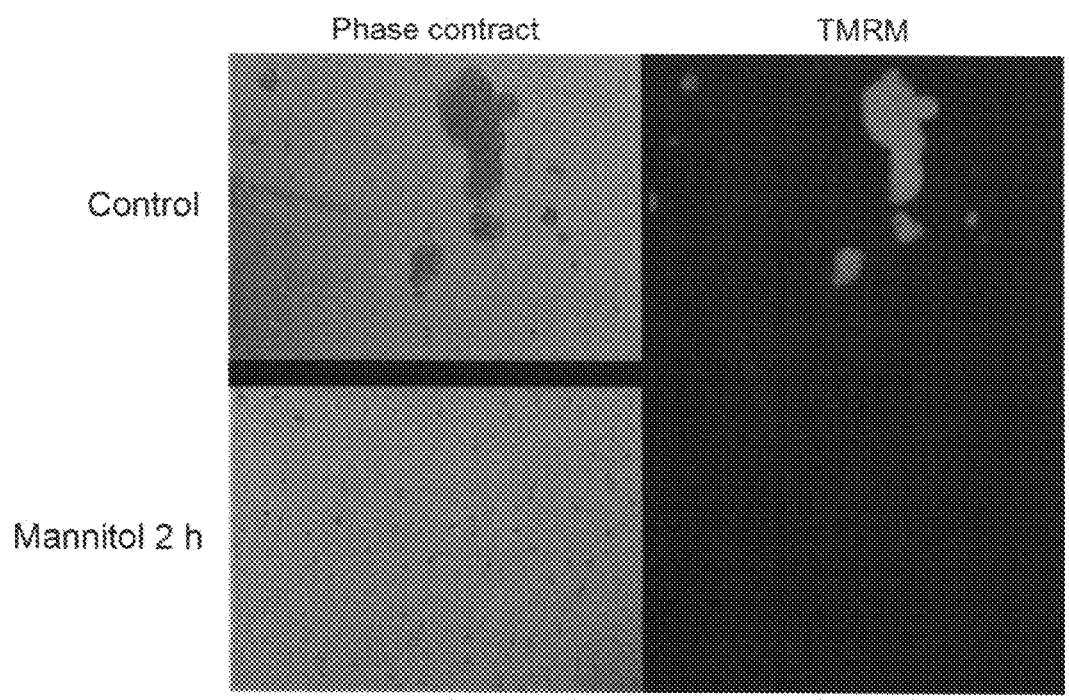
FIG. 8 shows the effect of mannitol on human embryonic stem cells (immediately after the treatment).

In addition, the TMRM-stained cells were photographed, both for the case of 2-h treatment with mannitol and for the control (FIG. 8)). The cells not treated with mannitol (the upper panels of FIG. 8) had been aggregated with each other to form self-aggregating masses through intercellular adherence but the cells treated with mannitol (the lower panels of FIG. 8) remained dispersed (FIG. 8).

Figure 9:
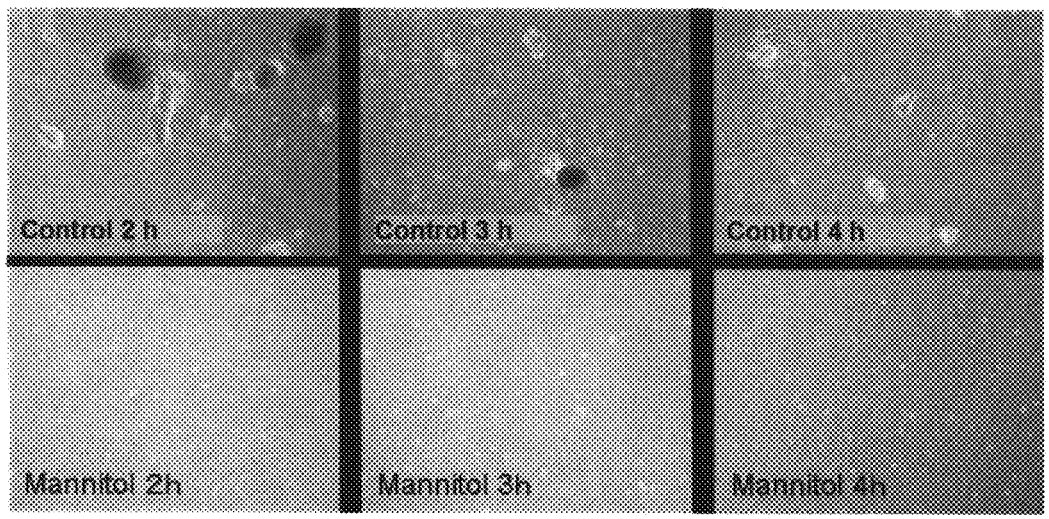
FIG. 9 shows the effect of mannitol on human embryonic stem cells (5 hours after the treatment).

Subsequently, the treated and control groups of cells were subjected to adherent culture for 5 days using a culture medium [F12/DMEM (1:1) (SIGMA; Product No. D6421), supplemented with 20% KO-SERUM (GIBCO), 1.6 mM L-glutamine, 0.1 mM non-essential amino acids (MEM), 0.1 mM (3-mercaptoethanol (2-ME; Sigma), 100 IU/ml penicillin, 100 μg/ml streptomycin sulfate, and recombinant human basic fibroblast growth factor (bFGF; Peprotech)]; as a result, large proportions of the control cells (i.e., cells not treated with mannitol) were found live (the upper panels of FIG. 9) but none of the cells exposed to mannitol were found live (the lower panels of FIG. 9).

Example 6

Cell Death Inducing Effect of Saccharides (Sugar Alcohols) on Residual Stem Cells in Human Embryonic Stem Cell-Derived Embryoid Bodies and Enrichment of Cardiomyocytes In this Example, cell masses (embryoid bodies) containing cardiomyocytes as formed from human embryonic stem cells were treated with saccharides (sugar alcohols) and subsequently checked for the state of culture of cardiomyocytes and that of other cells.

After passaging, human embryonic stem cells were subjected to suspension culture in a culture medium [α-MEM (minimum essential medium) (SIGMA), supplemented with 10% FBS (EQUITEC BIO), 100 units/ml penicillin, and 50 μg/ml streptomycin (GIBCO)] to induce formation of embryoid bodies. At 14-18 days after the start of differentiation (the start of suspension culture), autonomously pulsating cells started to differentiate, which was confirmed in a separate step that they were cardiomyocytes.

The embryoid bodies still maintained an autonomously pulsating ability after the passage of 3 months from the start of differentiation. They were partially treated with 0.1% collagenase (Wortington) and 0.1% trypsin (DIFCO) to be dispersed as fine cell masses. The cell masses were divided into two groups; one group was treated with 0.45 M mannitol (approximately equivalent to 720 mOsm/kg) for 2 hours, and the other group (control) was not treated with mannitol but treated with the same amount of a solution having the physiological osmotic pressure, Ads buffer (116.4 mM NaCl, 5.4 mM KCl, 5.6 mM dextrose, 10.9 mM $NaH_2PO_4$, 405.7 µM $MgSO_4$, 20 mM Hepes, pH 7.3) for 2 hours. After the treatment, both cell groups were subjected to adherent culture for 3 days in a DMEM solution supplemented with 10% fetal calf serum.

Three days later, both cell groups were observed under a microscope and in the culture dish for the cells of the control group, there were found a large number of colonies each consisting of a population of cells that were assumed to be undifferentiated cells in which the nucleus accounted for a larger area as compared with the cytoplasm. On the other hand, no such cell populations were found at all in the culture dish for the cells treated with mannitol.

Figure 10:
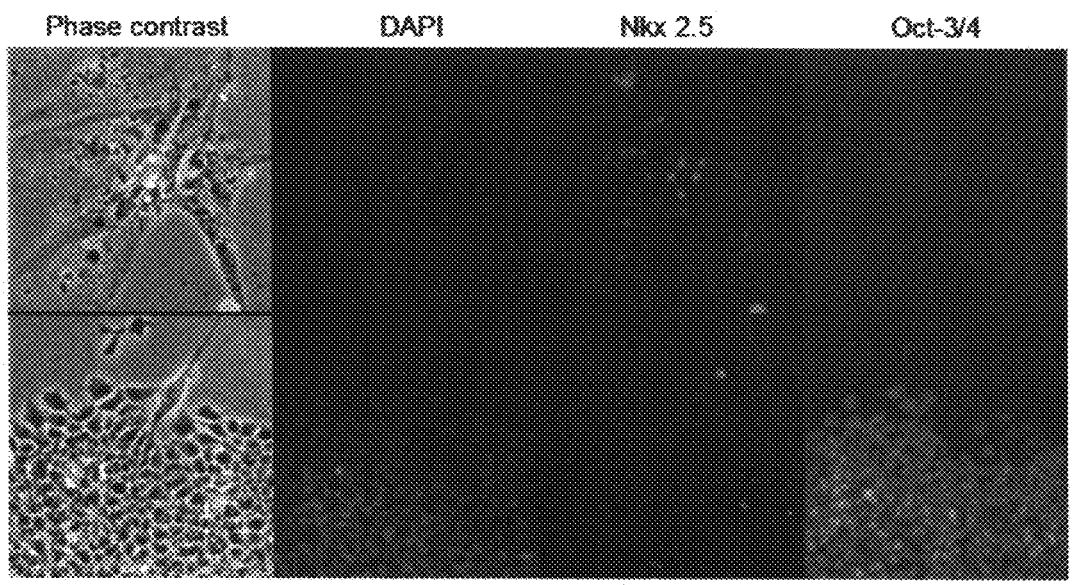
FIG. 10 shows the results of treating embryoid bodies of human embryonic stem cells with mannitol.
Figure 11:
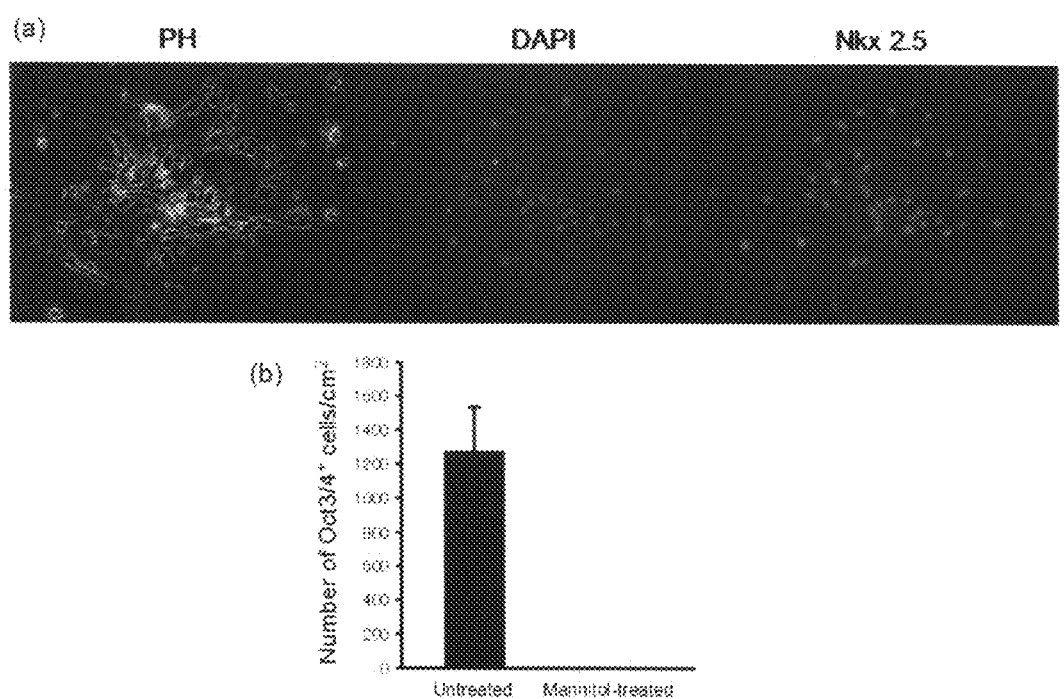
FIG. 11 shows induction of the cell death of Oct-3/4 positive cells due to treatment with mannitol of embryoid bodies of human embryonic stem cells.

Instead, autonomously pulsating cell populations and autonomously pulsating single cells were found adherent to or suspended in the culture dish for the cells treated with mannitol. The mannitol-treated cells and the control cells were analyzed in accordance with the experimental procedure of Example 1 using a mouse anti-Oct-3/4 monoclonal antibody (No. 084720 of BD Transduction Laboratories) and a goat anti-Nkx 2.5 antibody (No. N-19 of Santacruz) as primary antibodies, for the expression of the Oct-3/4 protein which was both a marker of embryonic stem cells and an intranuclear transcription factor, and for the expression of the Nkx 2.5 protein which was both a cardiomyocyte marker and an intranuclear transcription factor, respectively. The results for the control group, one of the two divided samples, are shown in FIG. 10 and the results for the test group subjected to 2-hr treatment with mannitol are shown in FIG. 11. The upper panels of FIG. 10 show the results of cardiomyocytes and the lower panels show the results of embryonic stem cells.

As a consequence, the colonies of embryonic stem cells-like cells that were found in great numbers in the control were Oct-3/4 positive, suggesting that they consisted of embryonic stem cells (the lower panels of FIG. 10). The autonomously pulsating cells that were found in the test group treated with 0.45 M mannitol (approximately equivalent to 720 mOsm/kg) were Nkx 2.5 positive and identified as cardiomyocytes (FIG. 11(a)). These results strongly suggest that the treatment with mannitol induces cell death in undifferentiated stem cells but does not show significant toxicity in cardiomyocytes (FIGS. 10 and 11).

The method of treatment under consideration was shown to be capable of efficiently inducing cell death of human embryonic stem cells. On the other hand, the method did not induce cell death in cardiomyocytes, showing its applicability as a method of enriching cardiomyocytes. One week after the treatment with mannitol, the type and the number of surviving cells were determined by an immunohistochemical technique; in contrast to the control cells (untreated group), a great majority of the surviving cells were Nkx 2.5 positive cardiomyocytes and Oct-3/3 negative cells were hardly detectable (FIG. 11(b)).

Example 7

Cell Death Inducing Effect of Saccharides (Sugar Alcohols) on Human Induced Pluripotent Stem Cells (iPS Cells)

In this Example, human induced pluripotent stem cells (iPS cells) were treated with saccharides (sugar alcohols) and subsequently checked for the state of their survival.

The human iPS cells were obtained from Stem Cell Research Center, Institute for Frontier Medical Sciences, Kyoto University (ES cell center sponsored by the National Bio-Resource Project). The cells were cultured basically in accordance with the same method as that in the case of human embryonic stem cells, i.e., in accordance with the same method as described in Example 5. After passaging, the cells were dispersed with each other using TE (0.25% trypsin (GIBCO) and 1 mM EDTA) and in accordance with a published document (Watanabe, K. et al., Nat. Biotechnol., 2007, 25: 681-686, Epub 2007 May 27), 10 µM of a ROCK inhibitor (Y27632) was added to suppress cell death. At the same time, the mitochondria in the live cells were stained with 50 nM TMRM.

Figure 12:
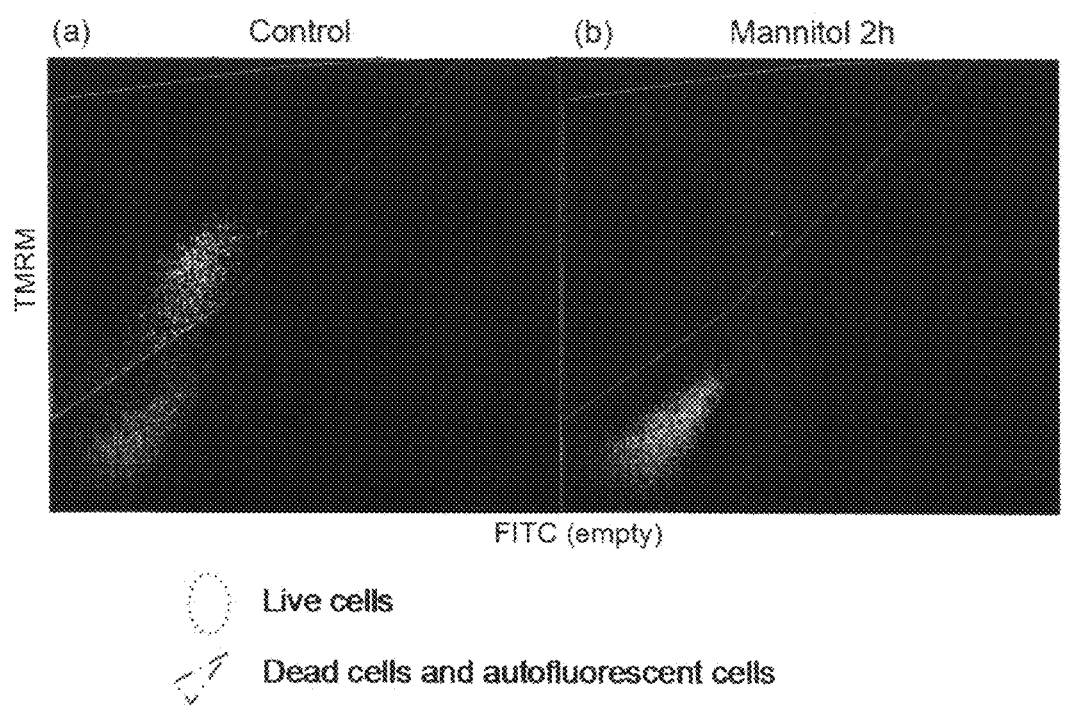
FIG. 12 shows the action of mannitol on human induced pluripotent stem cells (iPS cells) (by FACS analysis).

Part of the stained cells were treated with an α-MEM culture medium containing 0.45 M mannitol (approximately equivalent to 720 mOsm/kg) for 2 hours and a sample was prepared from these cells; the rest of the stained cells were treated with a mannitol-free α-MEM culture medium for 2 hours and a sample was prepared from these cells as a control. In the control, cells were aggregated with each other to make masses, so before FACS analysis, both samples were given another treatment with trypsin and EDTA to disperse the cells; thereafter, the samples were analyzed by FACS for the level of mitochondrial membrane potential on the basis of the fluorescent intensity of TMRM to check the state of survival of the stem cells; the results are shown in FIG. 12. As is clear from comparison with the control (FIG. 12(a)), almost all of the cells treated with mannitol for 2 hours had lost membrane potential (FIG. 12(b)). These cells were probably dead, as were the human embryonic stem cells.

Example 8

Cell Death Inducing Effect of Various Saccharides (Sugar Alcohols, Sugars, Betaines) on Human Embryonic Stem Cells In this Example, human embryonic stem cells were treated with saccharides other than mannitol (sugar alcohols, sugars, betaines) and subsequently checked for the state of their survival.

Figure 13:
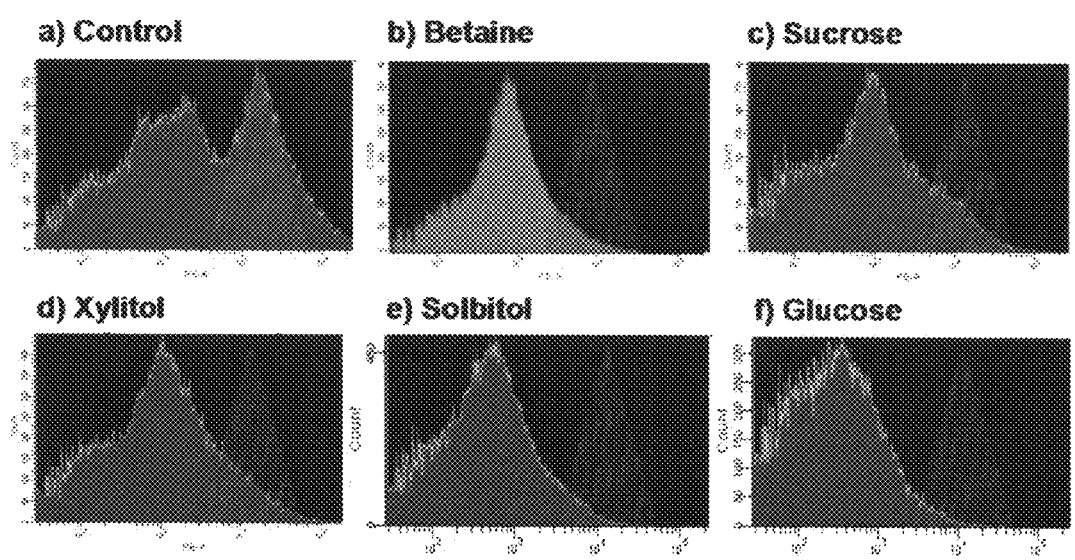
FIG. 13 shows the cell death inducing action of various saccharides other than mannitol on human embryonic stem cells.

Changes in the mitochondrial membrane potential were observed using the experimental technique of Example 5, provided that the human embryonic stem cells were treated not with mannitol, but with 0.45 M of various other saccharides (sugar alcohols: sorbitol and xylitol; sugars: sucrose and glucose; betaines: trimethylglycine) (approximately equivalent to 750-780 mOsm/kg) for 2 hours. The results are shown in FIG. 13. As is clear from comparison with the control (FIG. 13(a)), all of the cells treated with the above-mentioned saccharides for 2 hours had lost membrane potential (FIGS. 13(b)-(f)).

Example 9

Cell Death Inducing Effect of Various Saccharides (Sugar Alcohols, Sugars, Betaines) on Residual Stem Cells in Human Embryonic Stem Cell-Derived Embryoid Bodies and Enrichment of Cardiomyocytes In this Example, cell masses (embryoid bodies) containing cardiomyocytes as formed from human embryonic stem cells were treated with saccharides other than mannitol (sugar alcohols, sugars, betaines) and subsequently checked for the state of culture of cardiomyocytes and that of other cells.

After passaging, human embryonic stem cells were subjected to suspension culture in a culture medium [α-MEM (minimum essential medium) (SIGMA), supplemented with 10% FBS (EQUITEC BIO), 100 units/ml penicillin, and 50 μg/ml streptomycin (GIBCO)] to induce formation of embryoid bodies. At 14-18 days after the start of differentiation (the start of suspension culture), autonomously pulsating cells started to differentiate, which was confirmed in a separate step that they were cardiomyocytes.

The embryoid bodies still maintained an autonomously pulsating ability after the passage of 3 months from the start of differentiation. They were partially treated with 0.1% collagenase (Wortington) and 0.1% trypsin (DIFCO) to be dispersed as fine cell masses. The cell masses were divided into two groups; one group was treated with saccharides (sugar alcohols: sorbitol, xylitol, and glycerol; sugars: sucrose and glucose; betaines: trimethylglycine) for 12 hours in an amount of 0.45 M (approximately equivalent to 700-780 mOsm/kg) or 0.6 M (approximately equivalent to 850-1000 mOsm/kg), and the other group (control) was not treated with those saccharides but treated with the same amount of a solution having the physiological osmotic pressure, Ads buffer (116.4 mM NaCl, 5.4 mM KCl, 5.6 mM dextrose, 10.9 mM $NaH_2PO_4$, 405.7 μM $MgSO_4$, 20 mM Hepes, pH 7.3) for 2 hours. After the treatment, both cell groups were cultured for 12 hours in a DMEM solution supplemented with 10% fetal calf serum.

Twelve hours later, both cell groups were observed under a microscope and in the culture dish for the cells of the control group, there were found a large number of colonies each consisting of a population of cells that were assumed to be undifferentiated cells in which the nucleus accounted for a larger area as compared with the cytoplasm. On the other hand, no such cell populations were found at all in the culture dishes for the cells treated with the saccharides. Instead, autonomously pulsating cell populations and autonomously pulsating single cells were found adherent to or suspended in the culture dishes for the cells treated with the saccharides.

Example 10

Histological Analysis of Cell Death Inducing Effect of Saccharides (Sugar Alcohols) on Residual Stem Cells in Human Embryonic Stem Cell-Derived Embryoid Bodies In this Example, cell masses (embryoid bodies) containing cardiomyocytes as formed from human embryonic stem cells were treated with saccharides (sugar alcohols) and subsequently checked for the morphology of cells under the culture conditions for cardiomyocytes.

Figure 14:
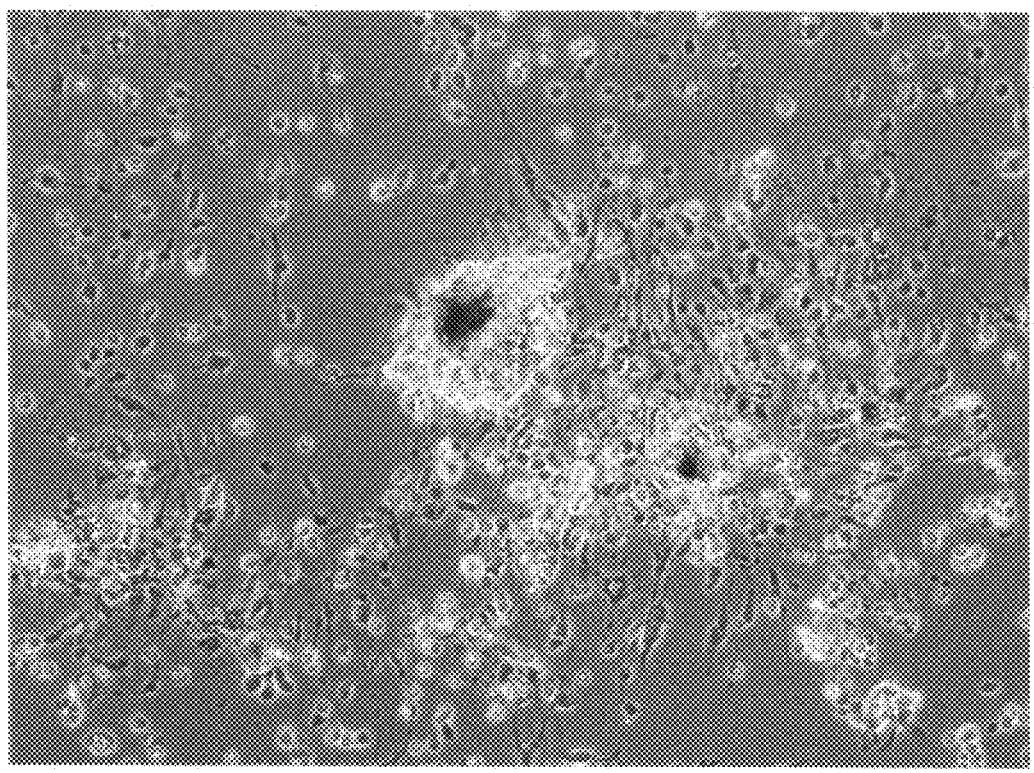
FIG. 14 shows the action of glycerol on human embryonic stem cell-derived cardiomyocytes and non-cardiomyocytes.

Samples of differentiated cells derived from human embryonic stem cells, as treated with 0.45 M glycerol (approximately equivalent to 710 mOsm/kg) or 0.6 M glycerol (approximately equivalent to 870 mOsm/kg), were examined for their morphology under the culture conditions. As it turned out, almost all of the differentiated cells other than cardiomyocytes had been dead. The cell death inducing effect was noticeable when the cells were exposed to glycerol for 10 hours and longer (FIG. 14).

From the foregoing results, it was found that prolonged treatment with glycerol would effectively induce cell death in pluripotent stem cells (embryonic stem cells/iPS cells) and differentiated cells other than cardiomyocytes.

Example 11

Cell Death Inducing, Effect of Low-Concentration Saccharide (Mannitol) on Mouse Embryonic Stem Cells In this Example, mouse embryonic stem cells were treated with a low concentration of mannitol and subsequently checked for the state of their survival.

Figure 15:
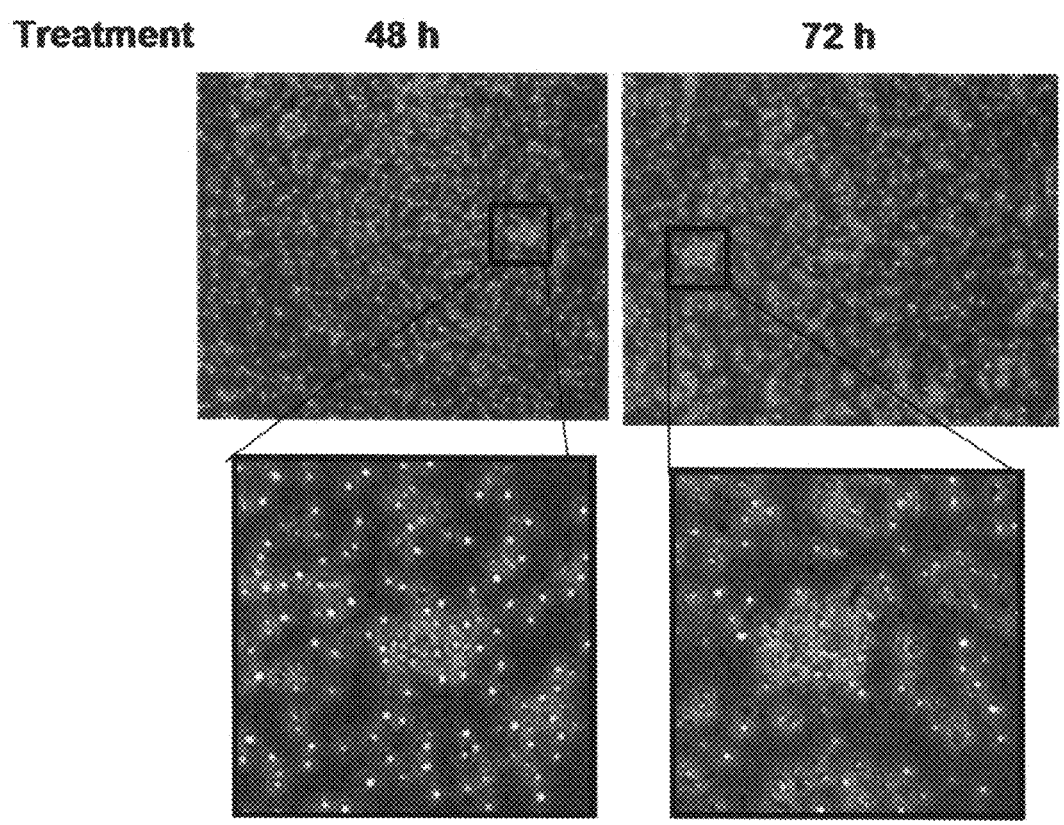
FIG. 15 shows the state of cells subjected to 48- or 72-hr treatment with a culture medium containing 0.2 M mannitol, with the images of respective colonies being enlarged in the lower panels to visualize typical cell morphology.

Embryonic stem cells as cultured by the method described in Example 1 were cultured for an additional 48 or 72 hours in an α-MEM culture medium containing 0.2 M mannitol (approximately equivalent to 480 mOsm/kg); thereafter, the stem cells were checked for the state of their survival in terms of cell adhesion or non-adhesion and by morphological observation; the results are shown in FIG. 15.

As FIG. 15 reveals, after the passage of 48 hours of treatment, almost all colonies had already detached from the culture dish to demonstrate the characteristic morphology of cell death. After 72 hours, this situation was more marked and the cells were completely dead. The discrete points shown in the photograph taken after 48 hours of treatment (labeled 48 h) and the photograph taken after 72 hours of treatment (labeled 72 h) represent individual cells. Also shown in each photograph are dead cell masses derived from a colony of ES cells. A typical example of such dead cell masses is shown enlarged below each photograph.

Additionally, similar to the method described in Example 1, 75 mouse embryonic stem cells per EB were cultured as cell masses for a total of 7 days by the hanging-drop technique using a culture medium [α-MEM (minimum essential medium) (SIGMA), supplemented with 10% FBS (EQUITEC BIO), 100 units/ml penicillin, and 50 μg/ml streptomycin (GIBCO)], whereby the stem cells were differentiated into cell masses containing cardiomyocytes; thereafter, the embryoid bodies were adhered to the culture dish and cultured for another 3-5 days under the conditions of 37° C. and 5% $CO_2$. The cardiomyocyte containing mouse embryoid bodies thus obtained by induction for differentiation and subsequent adherent culture were treated with 0.2 M mannitol for a period of up to 72 hours; after the passage of 72 hours, almost all cells other than cardiomyocytes had died and only the cardiomyocytes survived selectively, verifying the induction of cell death in the differentiated cells other than cardiomyocytes.

INDUSTRIAL APPLICABILITY

By applying the method of the present invention to treat a cell population including pluripotent cells, cells other than cardiomyocytes derived from pluripotent stem cells, and pluripotent stem cell-derived cardiomyocytes, the embryonic stem cells and cardiomyocytes in the cell population can be removed efficiently and, at the same time, only cardiomyocytes can survive, allowing for efficient enrichment and purification of the cardiomyocytes.

The invention claimed is:

1. A method for selecting for cardiomyocytes derived from pluripotent stem cells comprising culturing a population of cells including pluripotent stem cells, cardiomyocytes, and other cells derived from the pluripotent stem cells in a hypertonic solution having an osmotic pressure of 370 mOsm/kg or higher, wherein cell death is induced in non-cardiomyocyte cells.

2. The method according to claim 1, wherein culturing is conducted in the hypertonic solution for 2 hours or longer.

3. The method according to claim 1, wherein the hypertonic solution is prepared by adding a saccharide to a culture medium.

4. The method according to claim 3, wherein the hypertonic solution comprises 0.1-1 M saccharides.

5. The method according to claim 3, wherein saccharides are sugar alcohols, sugars, or betaines.

6. The method according to claim 5, wherein the sugar alcohols, sugars, or betaines are mannitol, sorbitol, xylitol, glycerol, sucrose, glucose, trimethylglycine, or combinations thereof.

7. The method according to claim 4, wherein the hypertonic solution comprises 0.1-0.6 M glycerol.

8. The method according to claim 7, wherein culturing is conducted for 10 hours or longer.

9. The method according to claim 1, further comprising returning the cell population, that has been cultured in the hypertonic solution, to a culturing medium having the normal osmotic pressure of 200-300 mOsm/kg and subjecting the cell population to further culturing.

10. The method of claim 3, wherein the saccharide is a carbohydrate.

11. A method for inducing cell death in a cell population comprising pluripotent stem cells and cardiomyocytes derived from pluripotent stem cells comprising culturing said cell population in a hypertonic solution having an osmotic pressure of 370 mOsm/kg or higher, wherein said pluripotent stem cells die and the cardiomyocytes derived from pluripotent stem cells do not die.

* * * * *